(12) United States Patent
Lindhofer et al.

(10) Patent No.: US 9,772,327 B2
(45) Date of Patent: Sep. 26, 2017

(54) INITIAL RELATIVE LYMPHOCYTE COUNT AS PREDICTIVE BIOMARKER

(75) Inventors: Horst Lindhofer, Munich (DE); Markus Heiss, Cologne (DE); Michael Stroehlein, Cologne (DE)

(73) Assignees: Markus Heiss, Cologne (DE); Michael Stroehlein, Cologne (DE)

( * ) Notice: Subject to any disclaimer, the term of this patent is extended or adjusted under 35 U.S.C. 154(b) by 849 days.

(21) Appl. No.: 14/118,213

(22) PCT Filed: May 16, 2012

(86) PCT No.: PCT/EP2012/059078
§ 371 (c)(1),
(2), (4) Date: Jul. 17, 2014

(87) PCT Pub. No.: WO2012/156429
PCT Pub. Date: Nov. 22, 2012

(65) Prior Publication Data
US 2015/0037278 A1 Feb. 5, 2015

(30) Foreign Application Priority Data
May 17, 2011 (EP) .................................... 11166403

(51) Int. Cl.
| | | |
|---|---|---|
| *A61K 39/395* | (2006.01) | |
| *A61K 38/00* | (2006.01) | |
| *G01N 33/50* | (2006.01) | |
| *G01N 33/574* | (2006.01) | |
| *C07K 16/28* | (2006.01) | |
| *C07K 16/30* | (2006.01) | |
| *A61K 38/20* | (2006.01) | |
| *A61K 39/00* | (2006.01) | |

(52) U.S. Cl.
CPC ..... *G01N 33/5094* (2013.01); *A61K 38/2013* (2013.01); *A61K 39/39558* (2013.01); *C07K 16/28* (2013.01); *C07K 16/2809* (2013.01); *C07K 16/30* (2013.01); *G01N 33/505* (2013.01); *G01N 33/574* (2013.01); *A61K 2039/505* (2013.01); *C07K 2317/31* (2013.01); *G01N 2800/52* (2013.01)

(58) Field of Classification Search
None
See application file for complete search history.

(56) References Cited

FOREIGN PATENT DOCUMENTS

| | | |
|---|---|---|
| EP | 2241576 A1 | 10/2010 |
| WO | 2008/040045 A1 | 4/2008 |

OTHER PUBLICATIONS

Kiewe, et al., "Phase I Trial of the Trifunctional Anti-HER2 X Anti-CD3 Antibody Ertumaxomab in Metastatic Breast Cancer," *Clin Cancer Res*, vol. 12(10), pp. 3085-3091 (2006).
Ruf, et al., "Two New Trifunctional Antibodies for the Therapy of Human Malignant Melanoma," *Int. J. Cancer*, vol. 108, pp. 725-732 (2004).
Ruf, et al., "Characterisation of the new EpCAM-specific antibody HO-3: implications for trifunctional antibody immunotherapy of cancer," *British Journal of Cancer*, pp. 1-7 (2007).
Schuster, et al., "Immunotherapy with the trifunctional anti-CD20 x anti-CD3 antibody FBTA05 (Lymphomun) in paediatric high-risk patients with recurrent CD20-positive B cell malignancies," *British Journal of Haematology* pp. 1-13 (2014).
Stanglmaier, et al., "Bi20 (FBTA05), a novel trifunctional bispecific antibody (anti-CD20 x anti-CD3), mediates efficient killing of B-cell lymphoma cells even with very low CD20 expression levels" *Int. J. Cancer*, vol. 123, pp. 1181-1189 (2008).
Fumagalli, et al., "Lymphocyte Counts Independently Predict Overall Survival in Advanced Cancer Patients: A Biomarker for IL-2 Immunotherapy," *Journal of Immunotherapy*, vol. 26(5), pp. 394-402 (2003).
Seimetz, et al., "Development and approval of the trifunctional antibody catumaxomab (anti-EpCAM x anti-CD3) as a targeted cancer immunotherapy," *Cancer Treatment Reviews*, vol. 36(6), pp. 458-467 (2010).
Ströhlein, et al., "Induction of anti-tumor immunity by trifunctional antibodies in patients with peritoneal carcinomatosis," *Journal of Experimental & Clinical Cancer Research*, vol. 28(1), 10 pages (2009).
International Search Report and Written Opinion for PCT/EP2012/059078, 10 pages, mailed Jun. 21, 2012.

*Primary Examiner* — Michail Belyavskyi
(74) *Attorney, Agent, or Firm* — Kilpatrick Townsend & Stockton LLP (57) ABSTRACT

The invention relates to a method for predicting an improved therapeutic benefit for an individual with a tumor load before initiating an immune therapy which is capable of activating immune cells against said tumor as well as to pharmaceutical compositions for use in this method.

16 Claims, 7 Drawing Sheets

Bivariate adjustment of survival (in months) by RLC (in LY percent) after Catumaxomab treatment

Linear Adjustment: Months = 4,118271 + 0,3859576*LY percent

Figure 3

Bivariate correlation of survival (in months) and granulocyte count in percent

Bivariate Adjustment of MONTHS by Gran pro

——— linear adjustment

Linear Adjustment

MONTHS = 18,40912 - 0,1181089*Gran pro

Figure 4

Logistic Regression in % lymphocyte count in categories >11%, >12% and >14%

INITIAL RELATIVE LYMPHOCYTE COUNT AS PREDICTIVE BIOMARKER

CROSS-REFERENCE TO RELATED APPLICATIONS

This application is the U.S. National Stage entry of PCT/EP2012/059078, filed May 16, 2012, which claims priority to European Application No. 11166403.3, filed May 17 2011, which are incorporated in their entirety herein.

FIELD OF THE INVENTION

The invention relates to a method for predicting an improved therapeutic benefit for an individual with a tumor load before initiating an immune therapy which is capable of activating immune cells against said tumor as well as to pharmaceutical compositions for use in this method.

BACKGROUND OF INVENTION

Modern therapeutic concepts for the treatment of tumors and particularly therapeutic concepts involving immune modulating agents involve considerable costs and often adverse side effects for the patient. Additionally not only one but several options for therapy or even due to bad prognostic effect the option of not actively treating the tumor but taking only palliative care of the patient must be considered by the physician. Hence selecting the most optimal therapeutic concept by taking into consideration predictive parameters is of high importance.

Several predictive or prognostic factors are known in the art and are used by the physicians:
- clinical-morphological criteria: TNM classification, R classification
- histopathological criteria: histological grade of differentiation
- molecular factors related to the target structures of tumor therapy: rate of expression of receptors (e.g. Her2/neu—Trastuzumab) and molecular status of mutation (KRAS mutation—Cetuximab).

Widely used in the field of diagnostics and the surveillance of the effects of therapeutic developments e.g. in the treatment of infectious diseases, anemic diseases and leukemia is the determination of the white cell blood count (also called blood differential test). The blood differential test measures the percentage of each type of white blood cell (also called leukocytes). This complete white blood cell count, which includes a lymphocyte count (ALC and RLC), is part of normal diagnosis and is an inexpensive, non-sophisticated and universally available test. Five types of leukocytes normally appear in the blood, i.e. neutrophils (normal values from adults: 40% to 60%,) lymphocytes (15% to 40%), monocytes (2% to 8%), eosinophils (1% to 4%), basophils (0.5% to 1%).

Generally all kind of acute stress and all kind of infections raise the number of leukocytes. Abnormally high titers of leukocytes are seen inter alia during inflammation, immunological reactions and leukemia. Changes in the blood differential test results are caused by the increase of one type of white blood cells which causes a decrease in the proportion of the remaining types of white blood cells.

Thus, an increased RLC above normal ranges may be due to an acute stage of viral infection, connective tissue disease, hyperthyroidism, Addison's disease and splenomegaly) (Tefferi et al., Mayo Clin. Proc. 80:923, 2005). Moreover, it is normal that children younger than 2 years have increased RLC. On the opposite side, a decreased RLC could be attributed to e.g. AIDS, bone marrow suppression, aplastic anemia, neoplasms, steroids, adrenocortical hyperfunction, neurologic disorders (multiple sclerosis, myasthenia gravis, Guillain Barre syndrome) (Tefferi et al., Mayo Clin. Proc. 80:923, 2005), administration of steroid compounds and chronic inflammation reflecting a suppression of the immune system caused by said diseases.

Considering this, the blood differential test and the changes of the proportion of the individual components of white blood cells can be understood as a highly suitable method for monitoring the immunological status of an individual reflecting the relation of immunostimulatory and immunosuppressive factors.

In view of the importance of immunological parameters in cancer development and tumor progression, US 2010/0028932 and the underlying publication teach that baseline absolute lymphocyte counts (ALC) prior to therapeutic onset significantly influence overall survival of tumor patients. It provides methods for the prognostic impact of ALC and AGC (absolute granulocyte counts) on the overall survival of tumor patients independent of any particular medical treatment.

One important method for activating immune cells is administration of antibodies which are directed against a tumor-specific antigen, One example for the beneficial use of antibodies is administration of trifunctional bispecific (Triomab) antibodies which are characterized in that they bind at the same time (i) to the T cell receptor complex of a T cell, (ii) to tumor-associated antigens on a tumor cell, and (iii) via the Fc-portion of the trifunctional antibody, to Fcgamma-receptor I, IIa and/or III positive cells for the induction of anti-tumor immunity in humans and animals. They are described e.g. in U.S. Pat. No. 6,551,592. It is well-established knowledge that cytotoxic T cells stimulated by anti-CD3 triggering and co-stimulatory CD28-B7 interaction (i.e. via interplay of T cells and activating Fcgamma-receptor positive accessory cells) are the most important effector cells in the elimination of malignant target cells due to trifunctional bispecific antibodies. Furthermore, it is well-accepted that the mitogenic anti-CD3 binding arm of trifunctional antibodies together with co-stimulatory signals (delivered by accessory cells) evokes T cell activation subsequently followed by prominent T cell stimulation and/or T cell proliferation. These hematopoietic changes are central to the activity of mitogenic anti-CD3 antibodies as demonstrated by e.g. Schneider et al., Stem Cells 15:154, 1997.

Nevertheless, US 2010/0028932 neither gives any evidence on the role RLC and RGC might play in the development of tumor diseases nor describes predictive factors for beneficially using therapeutic interventions that clearly stimulate the T cell arm of cell-mediated immune responses against cancer.

It is an object of the present invention to provide reliable predictive factors for the benefit of an intervention of tumor patients by an immune therapy which is capable of activating immune cells.

SUMMARY OF THE INVENTION

This object is solved by a method for predicting an improved therapeutic benefit for an individual with a tumor load before initiating an immune therapy which is capable of activating immune cells against said tumor comprising
a. providing a blood sample of said individual before initiating said immune therapy;

b. determining the initial relative lymphocyte count (RLC) in said blood sample;
c. positively correlating said improved therapeutic benefit with increasing initial RLC values of greater than 11%.

Still further is provided a pharmaceutical composition comprising
a pharmaceutically effective amount of an agent which is capable of activating immune cells against a tumor,
and pharmaceutically acceptable carriers and/or excipients,
for use in a method of treatment of individuals suffering from said tumor with said agent wherein said individuals are selected before said treatment by the following method for predicting an improved therapeutic benefit for said individual with said tumor, comprising
a. providing a blood sample of said individual before initiating said immune therapy;
b. determining the initial relative lymphocyte count (RLC) in said blood sample;
c. positively correlating said improved therapeutic benefit with increasing initial RLC values of greater than 11%.

Further embodiments of the invention are described in the dependent claims and the following description in combination with the attached Figures and the Table.

The present inventors report here for the first time on a significantly strong correlation of an initial baseline RLC and RGC with predicting an overall survival of cancer patients upon treatment with a pharmaceutically effective amount of an agent which is capable of activating immune cells against a tumor. This finding is exemplified by treatment with an antibody which is capable of stimulating T cells and/or T cell proliferation, namely a Triomab-based treatment regime (here anti-EpCAM×anti-CD3 catumaxomab) which has enabled the inventors to generalize the finding to all agents capable of activating immune cells against a tumor, e.g. all kinds of antibodies capable of stimulating T cells and/or T cell proliferation, e.g. other kind of trifunctional bispecific antibodies as described herein. It is to be emphasized that the predictive method of the invention is independent from the type of immune treatment used. Therefore, the presently described antibody therapy is to be considered only as one example of an immune therapy activating immune cells which belong to the group of leukocytes. The method of the invention reflects for the first time the importance of the amount of RLC and RGC for predictive statements on the survival of patients with a tumor load when they undergo an immune therapy activating immune cells independent from the type of agent used for said immune stimulating therapy.

The Table and the Figures show:
Table 1: Recombinant bispecific antibodies developed for cellular cancer therapy and capable of being used in the methods of the invention.

DETAILED DESCRIPTION

Figure 1:
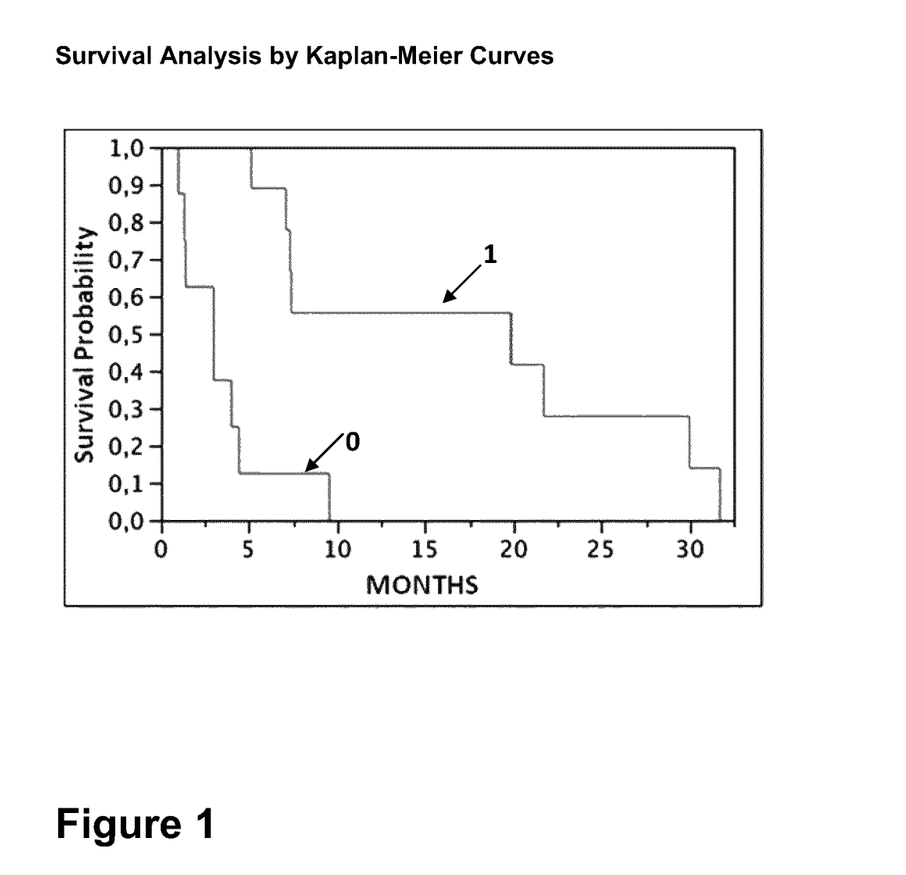
FIG. 1: Survival analysis by Kaplan-Meyer curves for patients with an RLC value of 11% or more. The following details are considered:
Time to progression: months
Censored with patient survives: y=1/n
Censor code: 1
Grouped by initial RLC>11% (P<0.05, log-rank or Wilcoxon test)
Figure 2:
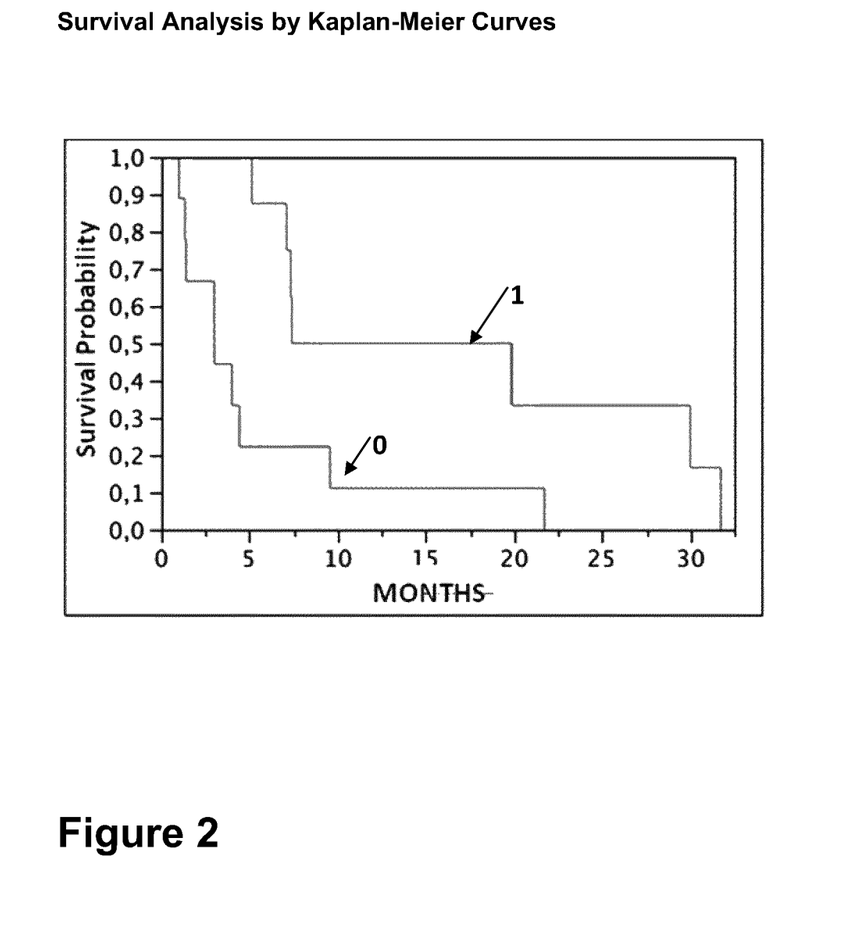
FIG. 2: Survival analysis by Kaplan-Meyer curves for patients with an RLC value of 14% or more. The following details are considered:
Time to progression: months
Censored with patient survives: y=1/n
Censor code: 1
Grouped by initial RLC>12% (P<0.05, log-rank or Wilcoxon test) or grouped by initial RLC>14% (P<0.05, log-rank or Wilcoxon test)
Figure 3:
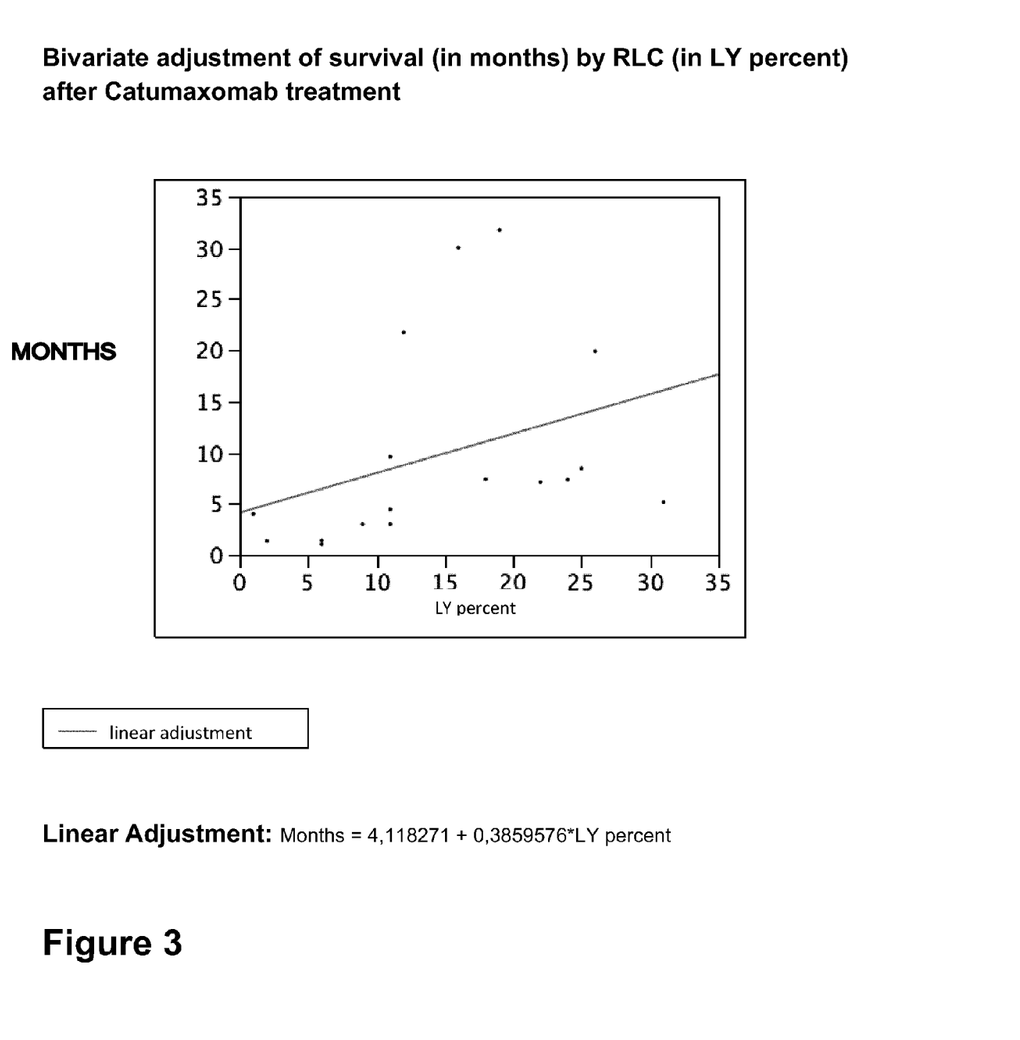
FIG. 3: Bivariate adjustment of survival (in months) by RLC (in LY percent)
Figure 4:
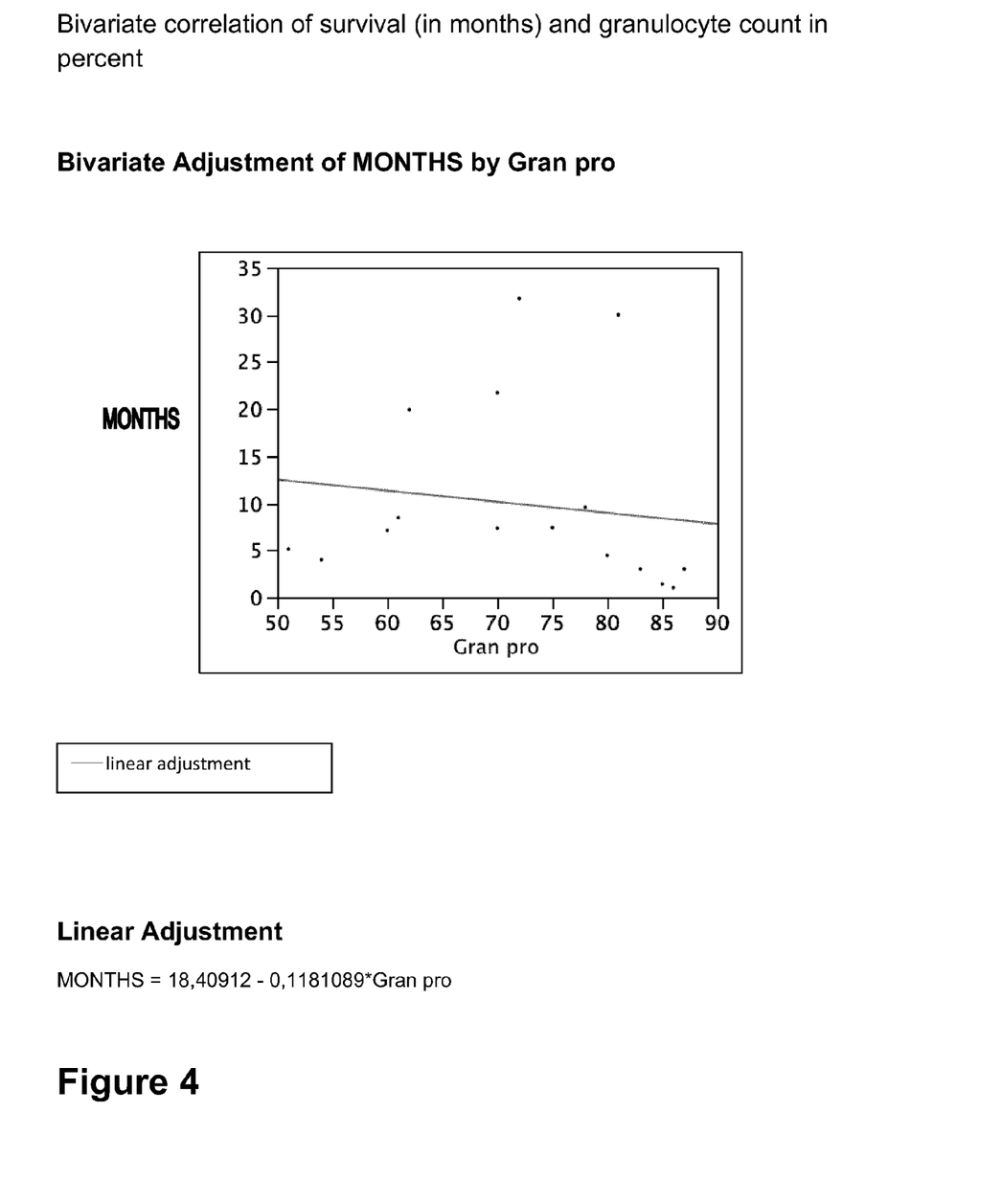
FIG. 4: Bivariate correlation of survival (in months) and granulocyte count in percent
Figure 5:
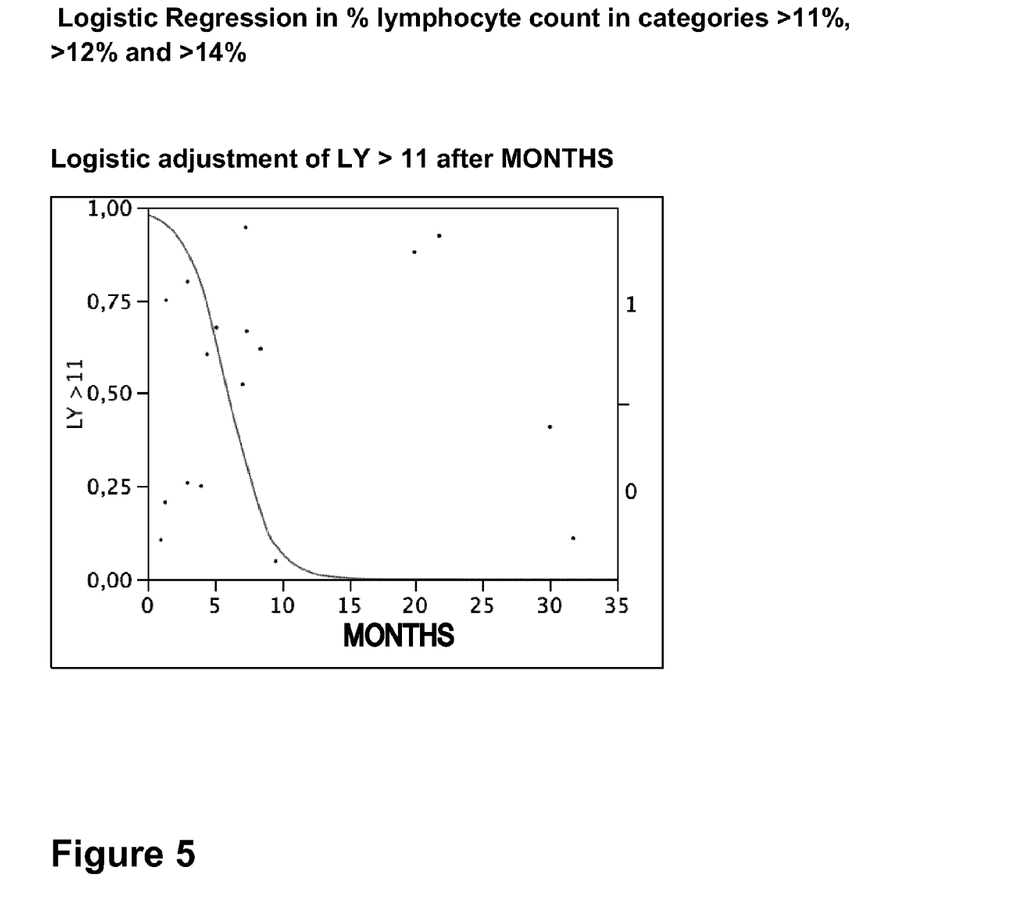
FIG. 5: Logistic Regression in % lymphocyte count in categories >11%, >12% and >14%
Figure 6:
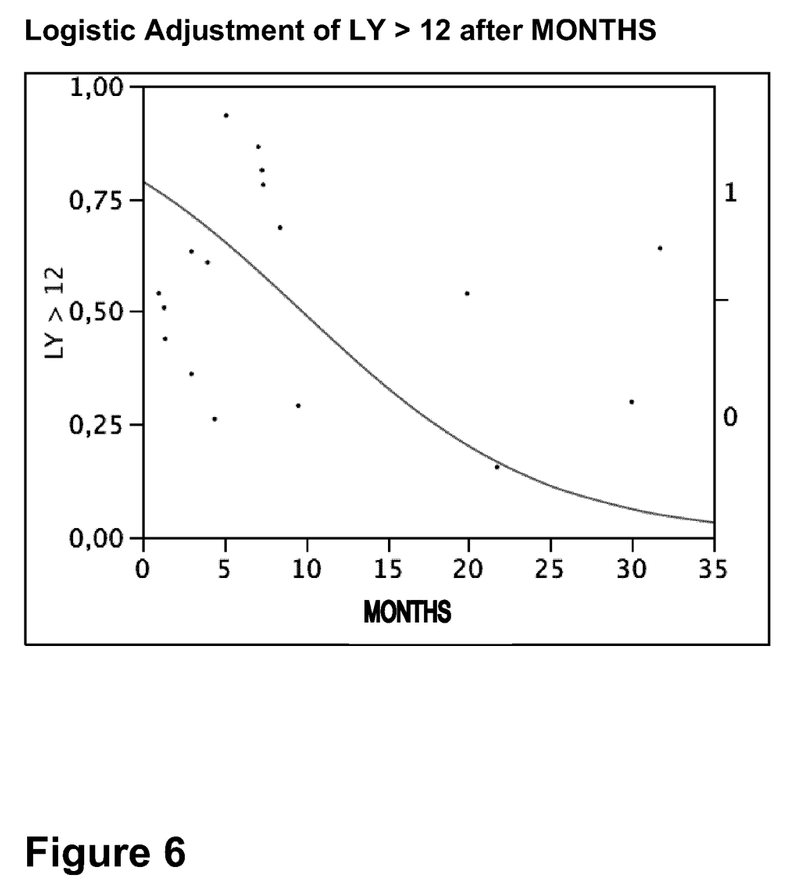
FIG. 6: Logistic Adjustment of LY>12 after MONTHS
Figure 7:
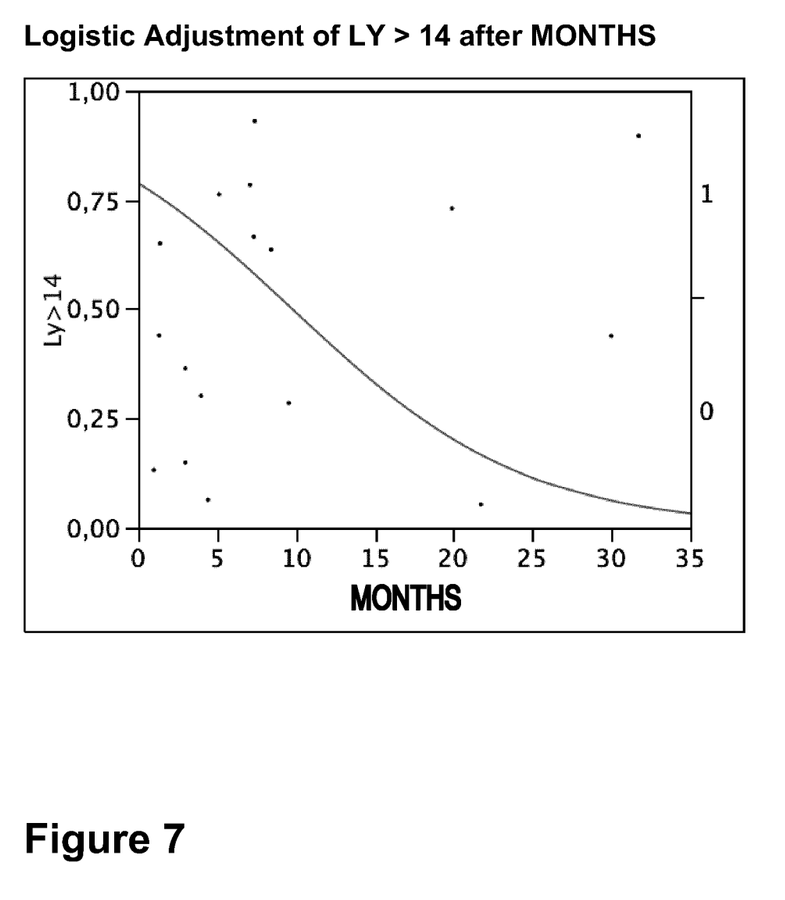
FIG. 7: Logistic Adjustment of LY>14 after MONTHS

As used herein, "absolute lymphocyte count" (ALC) refers to the total number of lymphocytes per unit of whole blood or blood cells. A unit can be, for example, a liter, milliliter, or microliter. ALC can be determined using a cell counting method that permits identification and quantitation of the total number of lymphocytes in a cell sample. The cell counting method can include, without limitation, fluorescent automated cell sorting (FACS), immunolabeling, and hematoxalin and eosin (H & E) staining, as well as any clinical instrument capable of accurately counting the number of lymphocytes in a blood sample. Such an instrument is, for example, the Beckman Coulter GEN S Cell system. Immunolabeled cell samples can be counted manually by one of skill in the art using a microscope at a magnification sufficient to permit visualization of immunolabeled cells versus non-immunolabeled cells. Immunolabeling refers to detection of a cell surface marker that is characteristic of a lymphocyte, such as the labeled antibody staining for cell surface markers described above. H & E stained cell samples also can be counted manually by one of skill in the art using a microscope at a magnification sufficient to permit visualization of the physical appearance of a lymphocyte.

It is a known medical diagnostic procedure to examine a dried, stained smear of blood on a microscope slide to determine the relative proportions of these five normal types of white blood cells, leukocytes: neutrophils, lymphocytes, monocytes, eosinophils and basophils. as well as the concentration of any abnormal cells. Such procedure is referred to as a differential white blood cell count and is described in Miale, J. B., "Laboratory Medicine—Hematology", pp. 822-830, 1126, 1127 and 1130, C. V. Mosby Company, St. Louis, Mo. (1967).

Automated processes and automated flow system apparatus therefore have been developed to ease the burden of differential white blood cell counting, such as described in U.S. Pat. Nos. 3,741,875 and 4,099,917. These are cytochemical procedures to specifically identify and label individual cell types.

The term "relative lymphocyte count" (RLC) refers to the percentage of lymphocytes in relation to the absolute number of leukocytes comprising neutrophils, monocytes, eosinophils, basophils and lymphocytes. Therefore, in order to determine the RLC value, the relative proportion of all 5 cell types as outlined above have to be measured and their percentage of the total number of leukocytes to be determined. The percentage is calculated as absolute lymphocyte count/total white blood cell count.

The term "relative granulocyte count" (RGC) refers to the percentage of granulocytes in relation to the absolute number of leukocytes comprising neutrophil granulocytes (also referred herein as "granulocytes" or "neutrophils"), monocytes, eosinophils, basophils and lymphocytes. Therefore, in order to determine the RGC value, the relative proportion of all 5 cell types as outlined above have to be measured and their percentage of the total number of leukocytes to be determined. The percentage is calculated as absolute granulocyte count/total white blood cell count.

Normal baseline absolute lymphocyte range of healthy individuals without obvious infectious diseases or other transient or chronic immunopathological alterations:

| Lymphocytes | number/mm$^3$ |
|---|---|
| Men | 1,000-4,000 (15-40%) |
| Women | 1,000-4,800 (15-50%) |
| Pregnancy | 1,300-5,200 (15-50%) |

White blood cell (WBC) determination is usually by hematology analyzers that produce fast and reliable data on blood count, while at the same time offering screening information on differential blood count (hematology analyzer of e.g. Cell-Dyn® 1700CS of Abbott Diagnostics; Petani et al., Clinical Chemistry 43:1085-1088, 1997 or Model S or Z2 Coulter Counter; Peng et al., *Int. J. Lab. Hematol.* 29(5):361-8; 2007). Summarizing, normal baseline RLC values are ranging from 15% up to 50%.

The inventors have found that these RLC and RGC different to normal value ranges should be taken into account for further considerations with individuals intended for treatment with a pharmaceutically effective amount of an agent which is capable of activating immune cells against a tumor. One exemplary example for said immune activating treatment are antibodies which are capable of stimulating T cells and/or T cell proliferation, specifically and preferably a trifunctional bispecific antibody therapy.

As used herein, "an agent which is capable of activating immune cells against a tumor" refers to reagents to stimulate the body's own immune system to fight a tumor disease. Inclusive herein are active immunotherapeutic agents, compositions or products with immunomodulating activities. Said agents include substances activating immune cells like T lymphocytes, B lymphocytes, monocytes, macrophages, dendritic cells etc. via e.g. receptor mediated contacts, cytokines or further mechanisms The inventors have surprisingly found that determination of RLC allows a reliable prediction of an improved therapeutic benefit for patient with a tumor load before initiating an immune therapy capable of activating immune cells. The term "therapeutic benefit" is to be understood as the patient's time period of surviving the tumor disease after said immune treatment. The inventors have found that said improved therapeutic benefit positively correlates with increasing initial RLC values of greater than 11%. The higher the initial RLC value is the higher the patient's prospect will be of surviving the immunostimulating tumor treatment. Depending on the individual patient and his disease or diseases and his overall immune situation, the lower limit of the initial RLC value is 11%. Higher RLC values of for instance 12 to 20%, 12 to 19%, 12 to 15%, 20 to 25%, 12 to 50% or even 12 to 70% identify patients with an improved therapeutic benefit, i.e. an extended survival time after having received said immune treatment. The lower border limits as identified above may be combined with any of the upper limits as defined herein above.

The inventors have surprisingly found that determination of initial RLC allows a reliable prediction of an improved therapeutic benefit for patients with a tumor load before initiating an immune therapy capable of activating immune cells. The term "therapeutic benefit" is to be understood as the patient's time period of surviving the tumor disease after said immune treatment. The inventors have found that said improved therapeutic benefit positively correlates with increasing initial RLC values of greater than 11%, in one embodiment of equal to or greater than 11%. The higher the initial RLC value is the higher the patient's prospect will be of surviving the immunostimulating tumor treatment. Higher RLC values of for instance 12 to 20%, 12 to 19%, 12 to 15%, 20 to 25%, 12 to 50% or even 12 to 70% identify patients with an improved therapeutic benefit, i.e. an extended survival time after having received said immune treatment. The lower border limit as identified above may be combined with any of the upper limits as defined herein above. Due to the variability of the overall immune situation among the individual patients, the figures described herein (above and below) with respect to the initial RLC and RGC values have to be understood as lying within certain ranges which are best to be expressed by the term "about".

The inventors have also found that the initial RGC values negatively correlate with the therapeutic benefit. The higher the initial RGC is the lower will be the patient's survival time after having received said immune treatment. Generally the initial RGC value is between about 80 to 100%. Therefore, also the initial RGC value can be used as a reliable predictive marker for determining the patient's time period of surviving the tumor disease after said immune treatment.

In a still further embodiment of the invention, predictive parameters for preselecting individuals suffering from a tumor load are described whether or not they will gain a therapeutic benefit from a treatment by a pharmaceutically effective amount of an agent which is capable of activating immune cells against said tumor. Due to the high costs of immune modulating treatments a careful selection of those patients who will probably gain a sufficient benefit from the treatment is of utmost importance.

The inventors have found that those individuals with a tumor load can be preselected as being not suitable for said immune treatment if their initial RLC value is below a range of 11%.

The inventors have also found that those individuals with a tumor load can be preselected as being not suitable for said immune treatment if their initial RGC value is above 80%. Said value may differ from patient to patient and may be 80%, 82%, 83%, 84% or 85%. Preferably said border initial RGC value is 80%. Hence there is a negative correlation of the improved therapeutic benefit with said initial RGC value. The higher said initial RGC is the lower will be the patient's prospect of surviving the tumor after said immune treatment.

The initial RGC and RLC values discussed herein can be used independent from each other as prospective markers for predicting an improved therapeutic benefit for an individual with a tumor load before initiating an immune therapy which is capable of activating immune cells against said tumor. In a still further embodiment of the invention these perspective markers may be combined in order to further improve and refine said perspective conclusions.

As can be seen from the present description of the invention, the prospect of patients with high lymphocyte counts are improved. Therefore, it is of benefit for the individual to be treated to raise the lymphocyte counts before start of the immune therapy. In one embodiment of the invention the patient will be pre-treated before said immune therapy will be initiated in order to raise said lymphocyte counts. Said pre-treatment may include administration of lymphocytes or administration of lymphocyte increasing drugs including IL-2, thymopentin or a combination thereof. Further options to increase the number of lymphocytes are:

Antibody infusions to prevent CTLA-4 inhibitory effects
Antibody infusions to block PD-L1-PD-1 interactions and rejuvenate exhausted T cells
Antibody infusions to enhance 4-1BB signals
Cytokine administration, e.g. IL-7, IL-12, IL-15, or IL-21
Cytokine antagonists, e.g., TGF-b blockade or inhibition
The immunstimulants Zadaxin and β-glucans Specific Description of the Invention with Respect to Antibody Treatment In a particularly preferred embodiment of the invention patients with increasing initial RLCs ranging between about 12-50% benefit (i.e. have an improved time of survival) from a treatment with antibodies which are capable of stimulating T cells and/or T cell proliferation, specifically and preferably from Triomab antibody therapy. In further preferred embodiments of the invention, the RLC values are increasing between ranges of about 11 to 40%, 11 to 30%, 11 to 20% while the lower limit of the RLC values is 11%, increasing initial RLC values indicating an improvement in the patient's survival time after said immune treatment with said antibodies.

Specifically for patients who do not suffer from secondary diseases like an acute stage of viral infection, a Connective tissue disease, hyperthyreodism, Addison's disease or splenomegaly accompanied by immunopathological changes with increased RLC (>50%), initial RLC values of between 11 to 50% will be used for identifying individuals having a good prognosis for improved overall survival time and for an improved clinical benefit.

Increasing initial RGC values of 80% to 100% provide a worse predictic factor of survival for the patient to be treated according to the invention. Thus, already before therapy start initial RLC and initial RGC represent a positive and negative predictive value, respectively that allows a well-defined estimation whether patients will benefit from therapeutic interventions with antibodies capable of stimulating T cells and/or proliferation, specifically by trifunctional bispecific and trispecific antibodies.

Proof-of-concept of the present invention has been provided for the antibody catumaxomab (anti-EpCAM×anti-CD3) which belongs to the group of trifunctional bispecific antibodies which are characterized by the following features:

(a) binding to a T cell via CD3 and activating said T cell;
(b) binding to a tumor associated target antigen; and
(c) binding via its Fc-portion to Fcγ-receptor type I, IIa and/or III positive cells and initiating the production of cytokines or co-stimulatory signals or a combination thereof and thereby activating T cells.

Generally all kinds of tumor-associated target antigens can be used. Specific embodiments include target antigens associated with epithelial tumors, adenocarcinomas, colon carcinomas, mamma carcinomas, ovarial carcinomas, carcinomas of the lungs, and throat, nose and ear tumors. Furthermore, tumor-associated antigens of non-epithelial tumours like leukemias and lymphomas and virus inducted tumors like liver tumours or cervix carcinomas can be used. Examples for tumor-associated antigens to be used are MAGE-A3, NY-ESO-1, TRP2, gp100, Muc-1*, CEA, EpCAM, HER2/neu, GD2, GD3, CD20, G250, proteoglycans, MHCII, EGF-R, CD19, MUC-1, MUC-1*, Wue antigen, Lewis Y antigen, FAP, Pgp, MCSP, EpHA2, CD33, and the cell surface targets GC182, GT468, GT512.

The tumor-associated antigens described above are associated with or specific for particular tumors. E.g. EpCAM is typically associated with adeno carcinomas, Her2/neu with mamma carcinomas but also with colon, lung, gastric, pancreas and ovarian cancer, CD20 with B cell lymphomas like non-Hodgkin's lymphoma or chronic lymphatic leukemia, G250 with renal carcinomas, proteoglycans, GD3 and GD2 with melanomas, MHC II with B cell lymphomas and EGF-R and CEA with epithelial tumors.

According to the invention, heterologous intact trifunctional bispecific and/or trispecific antibodies (Triomab) are used in one specific and preferred embodiment of the invention. These antibodies are intact, i.e. have a functional Fc portion, and they must be heterologous in nature, i.e. they must consist of heavy immunoglobulin chains of different subclasses (subclass combinations, also fragments) and/or origin (species).

Activation of the Fcgamma-receptor-positive cells by Triomab depends on the subclass or subclass combination, respectively, of Triomab. As demonstrated in in vitro experiments, for example trifunctional bispecific antibodies of the subclass combination mouse lgG2a/rat lgG2b are able to bind simultaneously to and activate Fcgamma-receptor-positive cells leading to up-regulation and formation (expression), respectively, of co-stimulatory antigens, such as CD40, CD80, or CD86, on the cell surface of such cells.

While the trifunctional bispecific antibodies at the same time bind to and activate the T cell via one of binding arms (e.g. to CD3 or CD2), co-stimulatory signals derived from the Fcgamma-receptor-positive cell bound to the Fc-portion of the trifunctional bispecific antibody may be transferred to the T cell. I.e. only the combination of T cell activation via one binding arm of the trifunctional bispecific antibody and the concomitant transfer of co-stimulatory signals from the Fcgamma-receptor-positive cell to the T cell results in an effective T cell activation.

Binding of the Triomab antibodies preferably takes place via CD3, CD2, CD4, CD5, CD6, CD8, CD28, and/or CD44 to the T cell, most preferred via CD3. Fc☐-receptor-positive cells at least bear an Fcgamma receptor I, IIa, or III.

The antibodies employed according to the invention are able to bind to monocytes, macrophages, dendritic cells, "natural killer" cells (NK cells) and/or activated neutrophils all being Fcgamma receptor 1-positive cells.

The antibodies used according to the invention lead to an induction or increase in the expression of CD40, CD80, CD86, ICAM-1, and/or LFA-3 as co-stimulatory antigens and/or cytokine secretion by the Fcgamma-receptor-positive cell. The cytokines preferably are IL-1, IL-2, IL-4, IL-6, IL-8, IL-12, and/or TNF-[alpha].

Binding to the T cell takes place via the T cell receptor complex of the T cell.

Preferred are trifunctional antibodies with the following group of isotype combinations in its Fc-region:
rat-lgG2b/mouse-lgG2a,
rat-lgG2b/mouse-lgG2b,
rat-lgG2b/human-lgG1,
mouse-[VH-CH1,VL-CL]-human-lgG1/rat-[VH-CH1,VL-CL]-human-lgG1-[hinge]-human-lgG3*-[CH2-CH3]
wherein *=caucasian allotypes G3m(b+g)=no binding to protein A.

Preferably said trifunctional bispecific antibody is an anti-tumor associated target-antigen×anti-CD3 antibody binding to Fcgammaγ-type I//IIa/III-receptors with the isotype combination rat-lgG2b/mouse-lgG2a.

The antibodies are monoclonal, chimeric, recombinant, synthetic, semi-synthetic or chemically modified intact antibodies having for example Fv, Fab, scFv or F(ab)2 fragments.

The preparation of monoclonal antibodies preferably originating from mammals, e.g. methods, as for example described in Köhler and Milstein (Nature 256 (1975), 495), in Harlow and Lane (Antibodies, A Laboratory Manual (1988), Cold Spring Harbour) or in Galfré (Meth. Enzymol. 73 (1981), 3). Furthermore, it is possible to prepare the antibodies described by means of recombinant DNA technology according to techniques obvious to the skilled artisan (see Kurucz et al., J. Immunol. 154 (1995), 4576; Hollinger et al., Proc. Natl. Acad. Sc. USA 90 (1993), 6444). The antibodies used in the present method can be designed and manufactured by a person skilled in the art without undue burden. E.g. Greenwood et al. disclose the exchange of single immunoglobulin domains (for instance CH2) by suitable cloning technique. By using these cloning technique antibody combinations like mouse-[VH-CH1,VL-CL]-human-lgG1/rat-[VH-CH1,VL-CL]-human-lgG1-[hinge]-human-lgG3*-[CH2-CH3] wherein *=caucasian allotypes G3m(b+g)=no binding to protein A.

On the one hand, the preparation of trifunctional bispecific antibodies may be performed using recombinant DNA technology or by hybrid-hydridoma fusion technique (see for example Milstein et al., Nature 305 (1983), 537). By this technique, hybridoma cell lines producing antibodies each having one of the desired specificities are fused, and recombinant cell lines producing antibodies with both specificities are identified and isolated.

Generally all kinds of antibodies can be used as long as they are capable of induction of mitogenic T cell stimulation. Examples are any other lgG-like shaped chimeric antibodies with identical CD3 and Fc-receptor engagement but different third binding specificity which have the inherent capacity for mitogenic stimulation of T lymphocytes. Examples are bispecific antibody fragments with capability of binding to a T cell via CD3, and mitogenic therapeutic antibodies capable of stimulating T cells and/or T cell proliferation and binding to a surface antigen on T cells. Preferred recombinant bispecific antibodies which have been developed for cellular cancer therapy and which can be used within the scope of the invention are shown in the attached Table 1. Additional examples include anti-CD3 BiTE (bispecific T cell engager) antibodies e.g. Blinatumomab, MT110 (Baeuerle et al., Cancer Res. 2009, 4941-4944); Her2Bi, CD20Bi (Chames et al., Current Opinion in Drug Discovery&Development, 2009, 276-283); anti-CTLA4 Ipilimumab and Tremilimumab, (Nodi et al., 10.1056/NEJMoa1003466, 2010). A further article describing the antibodies which use is encompassed by the present claims is of Müller, D. et al., Curr. Opin. Mol. Therap. 2007, 319-326) All of these references are incorporated for full disclosure in their entirety.

Summarily, the present inventors have been able to convincingly show that increasing RLC values at therapy onset predicts a longer survival time for cancer patients before initiating an immune therapy which is capable of activating immune cells against said tumor, said immune therapy being for instance a therapy with trifunctional bispecific or trispecific antibodies, bispecific antibody fragments with CD3 engagement or mitogenic therapeutic antibodies in general that stimulate T cell induction and/or T cell proliferation. The disease control and survival upon treatment is associated with RLC. Accordingly, the survival of patients shows a statistically significant positive correlation with RLC. Patients with increasing RLCs ranging 11-50%, preferably 11-40%, further preferably 11-30% or 11-20%, and a lower limit of between a range of 11-15% (including 12%, 13%, 14%, 15%) showed a significantly increased overall survival. Thus, already before therapy start the initial RLC represents a positive predictive and prognostic marker value that allows a well-defined estimation whether patients will benefit from therapeutic interventions with e.g. antibody constructs capable of stimulating T cell proliferative responses.

It is to be understood that various modifications to the invention will be apparent to and can readily be made by those skilled in the art, given the disclosure herein, without departing from the scope and materials of this invention. The following examples are for purposes of illustration only and are not meant to limit the invention in any way.

Example

Catumaxomab (anti-EpCAM×anti-CD3) treatment of patients with peritoneal carcinomatosis (PC) of EpCAM-positive cancers was shown to be clinically effective in phase I and II studies and was approved in the EU for treatment of malignant ascites (Strohlein and Heiss, J. Surg. Oncol 100:329, 2009; Heiss et al., Int. J. Cancer 127:2209, 2010).

Methods

A pooled population of 17 patients with PC in an investigative and a phase I/II study with Catumaxomab treatment was assessed for RLC and absolute ALC lymphocyte counts, relative (RGC) and absolute granulocyte counts (AGC) before Catumaxomab therapy. The following statistical methods were used: Linear approximation, logistic regression, Kaplan-Meier curves, log-rank and Wilcoxon tests.

Results

Overall survival of PC patients showed a positive correlation with initial RLC of about 11% (P<0.05, log-rang or Wilcoxon test) upon Catumaxomab therapy. In contrast, initial ALC or relative and absolute granulocyte counts failed to show any statistically significant correlation with overall survival of PC patients. Thus, initial RLC was identified as potential prognostic and predictive parameter for superior disease control and survival after Catumaxomab treatment. RLC may be used as a biomarker to indicate a suitable immune status for Triomab therapy like Catumaxomab.

| | | | Description of Peritoneal Carcinomatosis (PC) Patients | | | | | | |
|---|---|---|---|---|---|---|---|---|---|
| Patients | Primary tumor of patients (pt)* | Pt survives y = 1/n | MONTHS | Responder | Leukocytes | RLC | ALC | RGC | AGC |
| TC | Gastric carcinoma | 0 | 1.3 | 0 | 15 | 2 | 0.3 | 85 | 12.75 |

-continued

| | | | | | | | | | |
|---|---|---|---|---|---|---|---|---|---|
| KG | Ovary carcinoma | 0 | 21.7 | 1 | 7.8 | 12 | 0.936 | 70 | 5.46 |
| ME | Cancer of unknown primary origin | 0 | 30.0 | 1 | 6.8 | 16 | 1.088 | 81 | 5.508 |
| JK | Gastric carcinoma | 0 | 7.1 | 1 | 5.6 | 22 | 1.232 | 60 | 3.36 |
| SJ | Gastric carcinoma | 0 | 19.9 | 1 | 4.3 | 26 | 1.118 | 62 | 2.666 |
| PR | Gastric carcinoma | 0 | 7.3 | 1 | 7.9 | 24 | 1.896 | 70 | 5.53 |
| WH | Gastric carcinoma | 1 | 8.4 | 1 | 10.5 | 25 | 2.625 | 61 | 6.405 |
| HP | Gastric carcinoma | 0 | 7.4 | 1 | 7.8 | 18 | 1.404 | 75 | 5.85 |
| JH | Ovary carcinoma | 0 | 5.1 | 1 | 6.5 | 31 | 2.015 | 51 | 3.315 |
| ME2 | Cancer of unknown primary origin | 0 | 31.7 | 1 | 6.2 | 19 | 1.178 | 72 | 4.464 |
| SR | Mamma carcinoma | 0 | 1.4 | 0 | 11.9 | 6 | 0.714 | 85 | 10.115 |
| SR2 | Ovary carcinoma | 0 | 9.6 | 0 | 4.7 | 11 | 0.517 | 78 | 3.666 |
| FH | Bronchial carcinoma | 0 | 4.4 | 0 | 10.5 | 11 | 1.155 | 80 | 8.4 |
| HC | Gastric carcinoma | 0 | 1.0 | 0 | 7.2 | 6 | 0.432 | 86 | 6.192 |
| WE | Gastric carcinoma | 0 | 3.0 | 0 | 19.6 | 9 | 1.764 | 87 | 17.052 |
| HF | Small intestine carcinoma | 0 | 4.0 | 0 | 10.7 | 1 | 0.107 | 54 | 5.778 |
| FG | Colon carcinoma | 0 | 3.0 | 0 | 11.6 | 11 | 1.276 | 83 | 9.628 |

Patients with peritoneal carcinomatosis and intraperitoneal immunotherapy with the trifunctional antibody catumaxomab
Responder: 1 = stable disease, partial regression or complete regression of cancer disease/0 = progressive disease
Leukocytes G/l
RLC = initial relative lymphocyte count analysed by differential blood test with venous peripheral blood taken before therapy
ALC = initial absolute lymphocyte count
RGC = initial relative granulocyte count analysed by differential blood test with venous peripheral blood taken before therapy
AGC = initial absolute granulocyte count

| Statistic Overview | | | | |
|---|---|---|---|---|
| Group | Number of patients | Number censored | Mean | Standard error |
| 0 | 8 | 0 | 3.46667 | 0.9799 |
| 1 | 8 | 1 | 17.3528 | 3.71275 |
| Combined | 16 | 1 | 10.6267 | 2.60604 |

| Quantile | | | | |
|---|---|---|---|---|
| Group | Median time | 95% CI bottom | 95% CI top | 25% failure | 75% failure |
| 0 | 3 | 1 | 4 | 1.3667 | 4.2167 |
| 1 | 19.9 | 5.1333 | 21.733 | 7.3333 | 30 |
| Combined | 7.1 | 3 | 9.5667 | 3 | 19.9 |

| Tests between groups | | | |
|---|---|---|---|
| Test | Chi$^2$ | Degrees of freedom | P >Chi$^2$ |
| Log-Rang | 11.4098 | 1 | 0.0007* |
| Wilcoxon | 11.3052 | 1 | 0.0008* |

TABLE 1

Recombinant bispecific antibodies developed for cellular cancer therapy.

| Trigger molecule | Target molecule | Antibody format | Efficacy demonstration | Possible indication |
|---|---|---|---|---|
| CD3 | CD19 | taFv (BiTE) | In vitro/in vivo | B-cell tumors |
| | CD19 | Db, scDb, TandAb | In vitro/in vivo | B-cell tumors |
| | CD20 | Db | In vitro/in vivo | B-cell tumors |
| | EpCAM | taFv (BiTE) | In vitro/in vivo | Various carcinomas |
| | EpCAM | taFv | In vitro/in vivo | Various carcinomas |
| | EpCAM | Db | In vitro | Various carcinomas |
| | HER2/neu | taFv | In vitro | Ovarian and breast cancer |
| | HER2/neu | Db | In vitro | Ovarian and breast cancer |
| | EGFR | Db | In vitro/in vivo | Various carcinomas |
| | EphA2 | taFv (BiTE) | In vitro/in vivo | Various carcinomas, metastatic melanoma |
| | CEA | Db | In vitro/in vivo | Various carcinomas |
| | CEA | scDb, scDb-HSA | In vitro | Various carcinomas |
| | Wue antigen | taFv (BiTE) | In vitro | Multiple myeloma |
| | MUC-1 | Db | In vitro/in vivo | Various carcinomas |
| | Lewis Y antigen | taFv | In vitro | Various carcinomas |
| | Pgp | Db | In vitro/in vivo | Drug-resistant cancers |
| | FAP | taFv | In vitro | Various carcinomas |
| | CD105 | scDb | In vitro | Solid tumors |

The invention claimed is:

1. A method for administering to an individual with a tumor load an immune therapy which is capable of activating immune cells against said tumor, said method comprising
   a. providing a blood sample of said individual before initiating said immune therapy;
   b. determining the initial relative lymphocyte count (RLC) in said blood sample;
   c. identifying said individual as one suitable to receive said immune therapy when the RLC value from step b is greater than 11%; and
   d. administering to said individual said immune therapy.

2. The method of claim 1, wherein said immune therapy is performed by administering an agent capable of stimulating T cells and/or leading to T cell proliferation, wherein said agent is an antibody which is capable of binding to a surface antigen on T cells and further stimulating T cells and/or leading to T cell proliferation.

3. The method of claim 2, wherein said antibody is selected from the group consisting of (1) trifunctional bispecific antibodies capable of binding to a T cell via CD3; binding to a tumor associated target antigen, and binding via their Fc-portion to Fcy-receptor type I, IIa and/or III positive cells; (2) bispecific antibody fragments with capability of binding to a T cell via CD3; (3) mitogenic therapeutic antibodies capable of stimulating T cells and/or leading to T cell proliferation and binding to a surface antigen on T cells, or a combination thereof.

4. The method according to claim 3, wherein said trifunctional antibody is a rat/mouse bispecific antibody.

5. The method according to claim 4, wherein said trifunctional antibody is selected from at least one member of the following group of isotype combinations in its Fc-region:
   rat-lgG2b/mouse-lgG2a,
   rat-lgG2b/mouse-lgG2b,
   rat-lgG2b/human-lgG1,
   mouse-[VH-CH1,VL-CL]-human-lgG1/rat-[VH-CH1, VL-CL]-human-lgG1-[hinge]-human-lgG3*-[CH2-CH3]
   wherein *=caucasian allotypes G3m(b+g)=no binding to protein A.

6. The method according to claim 3, wherein said tumor associated target antigen is selected from the group consisting of epithelial tumors, adenocarcinomas, colon carcinomas, mamma carcinomas, ovarian carcinomas, lung carcinomas, liver, brain or cervical tumors, non-epithelial tumors like leukemias or lymphomas, and virus induced tumors, wherein said tumor antigens are optionally selected from Her2/neu, CD20, EpCAM, GD2, GD3, G250, proteoglycans, MHC II, EGF-R, CEA, CD19, MUC-1, MUC-1*, Wue antigen, Lewis Y antigen, FAP, Pgp, MCSP, EpHA2, CD33, and the cell surface targets GC182, GT468, GT512.

7. The method according to claim 2, wherein said antibody is selected from the group consisting of anti-GD2× anti-CD3, anti-CD20×anti-CD3, anti-EpCAM×anti-CD3, anti-Her2/neu×anti-CD3, optionally with the isotype combination rat-lgG2b/mouse-lgG2a.

8. The method of claim 1, wherein step d comprises administering to the individual a pharmaceutical composition comprising a pharmaceutically effective amount of an agent which is capable of activating immune cells against a tumor, and pharmaceutically acceptable carriers and/or excipients.

9. The method of claim 8, wherein said agent is an antibody which is capable of binding to a surface antigen on T cells and further stimulating T cells and/or leading to T cell proliferation.

10. The method of claim 9 wherein said antibody is selected from the group consisting of (1) trifunctional bispecific antibodies capable of binding to a T cell via CD3; binding to a tumor associated target antigen, and binding via their Fc-portion to Fcy-receptor type I, IIa and/or Ill positive cells; (2) bispecific antibody fragments with capability of binding to a T cell via CD3; (3) mitogenic therapeutic antibodies capable of stimulating T cells and/or leading to T cell proliferation and binding to a surface antigen on T cells, or a combination thereof.

11. The method of claim 10, wherein said trifunctional antibody is a rat/mouse bispecific antibody.

12. The method of claim 11, wherein said trifunctional antibody is selected from at least one member of the following group of isotype combinations in its Fc-region:
   rat-lgG2b/mouse-lgG2a, rat-lgG2b/mouse-lgG2b, rat-lgG2b/human-lgG1, mouse-[VH-CH1,VL-CL]-human-lgG1/rat-[VH-CH1,VL-CL]-human-lgG1-[hinge]-human-lgG3*-[CH2-CH3]

wherein *=caucasian allotypes G3m(b+g)=no binding to protein A.

13. The method of claim 10, wherein said tumor-associated target antigen is selected from the group consisting of epithelial tumors, adenocarcinomas, colon carcinomas, mamma carcinomas, ovarian carcinomas, lung carcinomas, liver, brain or cervical tumors, non-epithelial tumors like leukemias or lymphomas, and virus-induced tumors, wherein said tumor antigens are optionally selected from Her2/neu, CD20, EpCAM, GD2, GD3, G250, proteoglycans, MHC II, EGF-R, CEA, CD19, MUC-1, MUC-1*, Wue antigen, Lewis Y antigen, FAP, Pgp, MCSP, EphA2, CD33, and the cell surface targets GC182, GT468, GT512.

14. The method of claim 11, wherein said antibody is selected from the group consisting of anti-GD2×anti-CD3, anti-CD20×anti-CD3, anti-EpCAM×anti-CD3, anti-Her2/neu×anti-CD3, optionally with the isotyp combination rat-lgG2b/mouse-lgG2a.

15. The method of claim 1, wherein before step a said individual has received pre-treatment in order to raise the number of lymphocytes.

16. The method of claim 15 wherein said pre-treatment includes administration of lymphocytes or administration of lymphocyte increasing drugs including IL-2, thymopentin or a combination thereof.

* * * * *